United States Patent [19]

Kalkkinen et al.

[11] Patent Number: 5,133,940

[45] Date of Patent: Jul. 28, 1992

[54] APPARATUS, FOR AMPLIFICATION OF NUCLEIC ACIDS

[75] Inventors: Nisse E. J. Kalkkinen; Hans E. Soderlund, both of Espoo, Finland

[73] Assignee: Orion Corporation Ltd., Finland

[21] Appl. No.: 285,804

[22] Filed: Dec. 16, 1988

[30] Foreign Application Priority Data

Dec. 23, 1987 [FI] Finland .................................. 875696

[51] Int. Cl.[5] ............................. C08F 3/00; B10J 8/00; C12M 1/38
[52] U.S. Cl. .................................... 422/138; 422/189; 422/203; 422/208; 435/290; 435/316; 935/88
[58] Field of Search ............... 435/290, 316, 513, 819; 935/85-88; 422/138, 189, 186.22, 186.25, 203, 208, 235, 146, 156; 137/571

[56] References Cited

U.S. PATENT DOCUMENTS

| | | | |
|---|---|---|---|
| 4,171,427 | 10/1979 | Ohorodnik et al. | 422/138 |
| 4,478,814 | 10/1984 | Kesten et al. | 422/189 |
| 4,683,194 | 7/1987 | Saiki et al. | 435/6 |
| 4,683,195 | 7/1987 | Mullis | 435/6 |
| 4,683,202 | 7/1987 | Mullis | 435/91 |
| 4,753,787 | 6/1988 | Krijgsman | 137/571 |
| 4,889,812 | 12/1989 | Guinn et al. | 435/813 |

FOREIGN PATENT DOCUMENTS

| | | |
|---|---|---|
| 0200362 | 3/1986 | European Pat. Off. |
| 0229701 | 1/1987 | European Pat. Off. |
| 0236069 | 2/1987 | European Pat. Off. |
| 0237362 | 3/1987 | European Pat. Off. |

OTHER PUBLICATIONS

Nucleic Acids Research vol. 16, No. 7, 1988 A Simple and Low Cost DNA Amplifier by Rolio et al., pp. 3105 and 3106.

DNA vol. 7, No. 6, 1988, pp. 441-447 Laboratory Methods-A Programmable System to Perform the Polymerase Chain Reaction by Heinz Ulrich and Joe W. Gray.

Polymerase chain reaction automated at low cost by N. S. Foulkes et al., pp. 5687-5688, Submitted May 17, 1988.

Primary Examiner—James C. Housel
Assistant Examiner—William K. Y. Chan
Attorney, Agent, or Firm—Brumbaugh, Graves, Donohue & Raymond

[57] ABSTRACT

Amplification of nucleic acids is performed by incubating in a polymerization vessel a reaction mixture which contains in a suitable buffer solution, one or several single-stranded target nucleic acids, suitable primers, deoxyribouncleoside triphosphates and a polymerase. After a sufficient time for polymerication to occur, the reaction mixture is transferred into another vessel for the denaturation of the nucleic acids into single stranded nucleic acids. After denaturation, the reaction mixture is transferred back into the original vessel. The amplification process is regulated to maintain a temperature advantageous for the action of the polymerization enzyme in the polymerization vessel and a temperature advantageous for denaaturation in the denaturation vessel. Furthermore, the apparatus includes a liquid transfer system for transferring the reaction liquid from one vessel to another, which comprises at least one liquid transfer tube per vessel pair which extends from within the polymerization vessel to within the denaturation vessel.

17 Claims, 4 Drawing Sheets

APPARATUS, FOR AMPLIFICATION OF NUCLEIC ACIDS

BACKGROUND OF THE INVENTION

The present invention relates to an apparatus and a method for performing automated amplification of nucleic acids under standardized conditions. The invention also relates to a disposable part for the apparatus used in the method.

The amplification of nucleic acids is described in U.S. Pat. No. 4,683,194, U.S. Pat. No. 4,683,195 and U.S. Pat. No. 4,683,202, and in patent applications EP 200 362, EP 229 701, EP 237 362 and U.S. 024 604. In amplification, a reaction mixture which contains the single-stranded target nucleic acid, at least two suitable primers, four different deoxyribonucleoside triphosphates, and DNA polymerase in a suitable buffer solution is first incubated at a suitable temperature in order to polymerize the DNA. Thereafter the double-stranded DNA formed in the polymerization is denatured by heating and the reaction mixture is cooled to a temperature at which the primers are capable of again hybridizing with the target DNA. When necessary, the temperature of the reaction mixture is adjusted to a temperature optimal for the action of DNA polymerase, and DNA polymerase is added. The steps described above are repeated as many times as is necessary for producing the desired result.

Amplification has in general been performed manually by transferring the test tubes from one place to another dozens of times. The method is slow and cumbersome to perform. When thermolabile polymerase has been used, it has been necessary to open and close the tubes at intervals. Furthermore, in order to produce a homogenous reaction fluid, it has been necessary to centrifuge from the walls of the tubes the reaction fluid condensed during the cooling step. It has been a further disadvantage that the reaction conditions vary during repeated steps. This has constituted a problem, especially when a thermostable enzyme has been used, since in spite of its thermostability the polymerase is destroyed if it is kept at a denaturation temperature for too long.

Patent application EP 236 069 describes an apparatus in which the amplification of nucleic acids is performed under computer control by heating and cooling the reaction mixture in the same vessel. This apparatus has certain disadvantages. It is difficult to heat and cool a reaction mixture with precision and with sufficient speed, since in addition to the temperature of the vessel and the reaction mixture in it, the temperature of the surrounding apparatus also has to be adjusted. The heat capacity of the surrounding apparatus is inevitably considerable compared with the heat capacity of the small-volume (approximately 100 $\mu$l) reaction mixture. For this reason, the reaction mixture is at a temperature which is disadvantageous for amplification for a significant portion of each cycle. Problems arise in particular in the controlling of the denaturation temperature and time. If the temperature is too low, denaturation will not proceed in the manner desirable with respect to amplification. On the other hand, if the polymerase has to be at or near the denaturation temperature for too long, even thermally stable polymerases will be destroyed. Thus, in practice, only a thermostable polymerase can be used and it is active for the duration of only a few reaction cycles.

For the reasons stated above it has not been possible to fully automate DNA amplification under standardized optimal conditions. The only automated system to date (described in EP 236,069) requires the use of a thermostable DNA polymerase and does not function under optimal conditions.

The object of the present invention is to provide an apparatus and method eliminating the above-mentioned disadvantages. By using the apparatus of the present invention it is possible to fully automate the amplification of nucleic acids in one or several samples simultaneously under standardized optimal reaction conditions. In the apparatus according to the invention, the correct denaturation temperature and time can be adjusted with sufficient precision and speed so as not to significantly denature thermally stable DNA polymerase. The method and apparatus according to the invention can be used for the amplification of nucleic acids regardless of whether the polymerase used is thermostable or not.

SUMMARY OF THE INVENTION

The invention relates to a method for performing the amplification of nucleic acids by incubating in a polymerization vessel a reaction mixture which contains in a suitable buffer solution, one or several single-stranded target nucleic acids, suitable primers, deoxyribonucleoside triphosphates and a polymerase. After a sufficient time for the desired amount of polymerization to occur, the reaction mixture is transferred into another vessel for the denaturation of the nucleic acids into single stranded nucleic acids. After denaturation, the reaction mixture is transferred back into the original vessel. The amplification process is regulated to maintain a temperature advantageous for the action of the polymerization enzyme in the polymerization vessel and a temperature advantageous for denaturation in the denaturation vessel. While transferring the reaction mixture from the denaturation vessel to the polymerization vessel the reaction mixture may pass through a heat exchanger. In the heat exchanger, the denatured reaction mixture is preferably cooled to a temperature at which the primers and the target DNA are capable of hybridizing.

The invention also relates to an apparatus for use in the method. The apparatus includes at least one pair of vessels. A vessel pair is made up of a polymerization vessel and a denaturation vessel. Each of the vessels is provided with a thermoregulator, for example a heat block provided with a thermostat, to maintain the temperature at a level appropriate for polymerization or denaturation, respectively. Furthermore, the apparatus includes a liquid transfer system for transferring the reaction liquid from one vessel to another, which comprises at least one liquid transfer tube per vessel pair which extends from within the polymerization vessel to within the denaturation vessel. A preferred liquid transfer system relies on a pressure differential between the vessel pair and includes a pair of gas supply tubes.

The apparatus may also be provided with a heat exchanger through which the liquid transfer tubes may pass, or the liquid transfer tube may itself serve as a heat exchanger if it is of sufficient length. Further, the vessel in which the polymerization occurs may also be equipped with a suitable dosing device for the addition of polymerase and/or reagents.

The disposable apparatus part of the invention includes, in packaged combination, a vessel pair and a liquid transfer tube sized for use in the apparatus of the invention. The vessel pair is advantageously adapted to receive and form an air tight seal with the gas tubes supply and dosing tubes of the apparatus, when a pressure differential liquid transfer system is used.

DESCRIPTION OF THE PREFERRED EMBODIMENT

Figure 1:
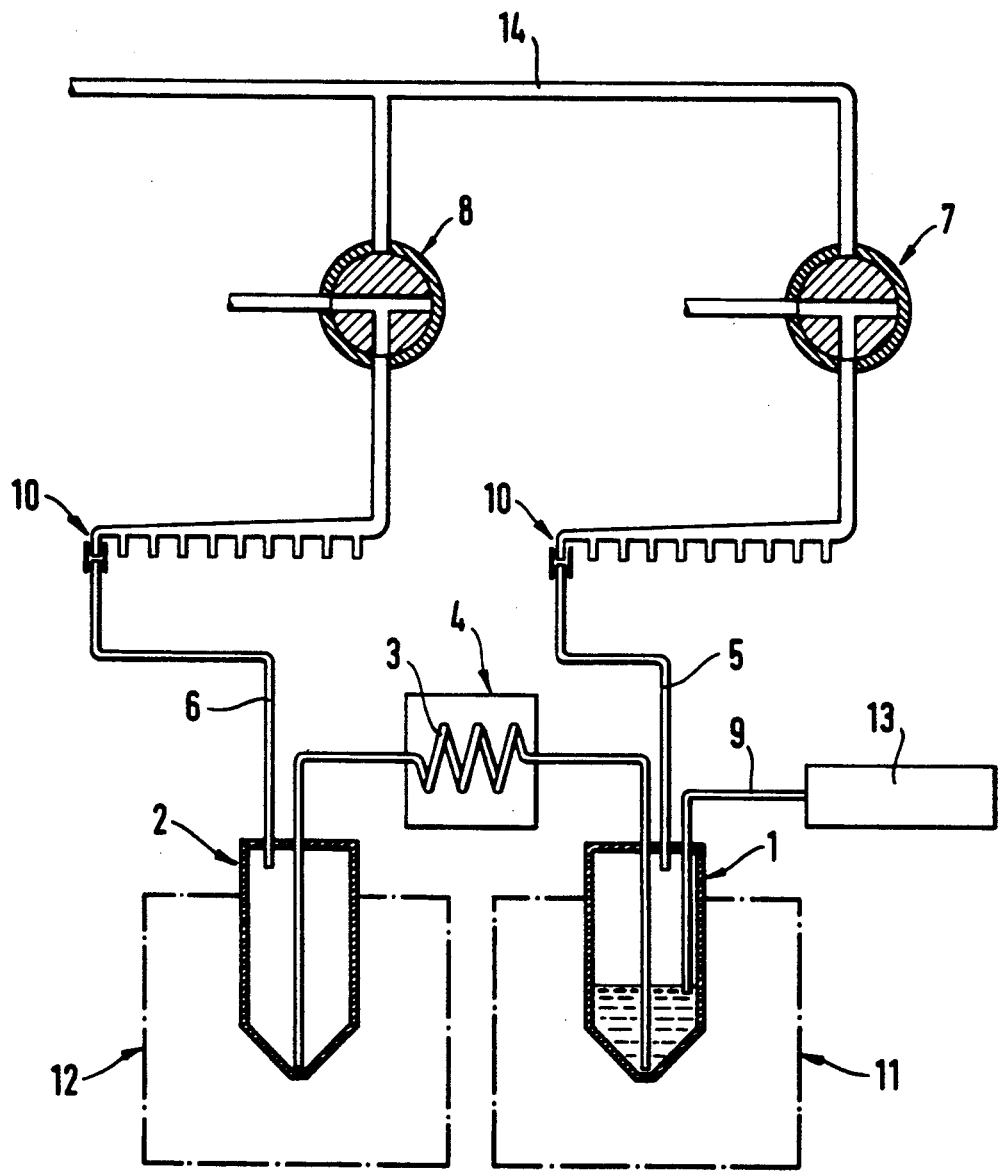
FIG. 1 depicts an apparatus according to the invention during the polymerization step of the method of the invention.
Figure 2:
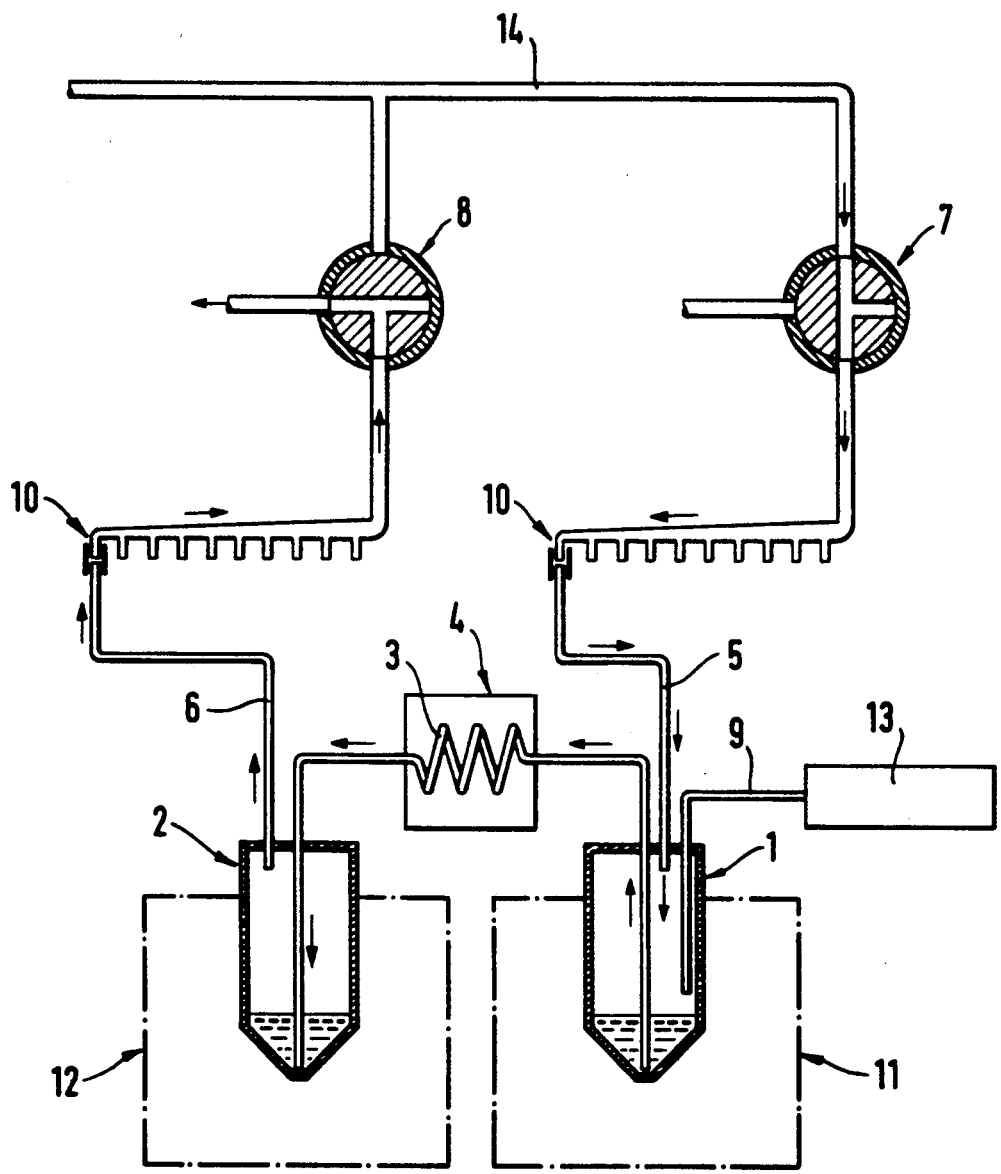
FIG. 2 depicts an apparatus according to the invention during the step of transferring the fluid into the denaturation vessel.

The method of the invention involves a number of cycles of polymerization and denaturation in order to produce an amplified sample from a starting sample containing single stranded nucleic acids. FIGS. 1 through 4 show one such cycle using an embodiment of the apparatus of the invention.

As shown in FIGS. 1 through 4, an embodiment of the apparatus of the invention comprises a polymerization vessel 1 and a denaturation vessel 2, disposed within thermoregulator means 11 and 12, respectively. Liquid transfer tube 3 extends from the interior of polymerization vessel 1 to the interior of denaturation vessel 2 and passes through heat exchanger 4. The end of the liquid transfer tube 3 should in each vessel extend to a point near the bottom of the vessel so that substantially the entire volume of liquid can be transferred from one vessel to the next. To optimize liquid transfer, the vessels will preferably have a substantially conical base portion extending downward from a substantially cylindrical top portion as shown in FIGS. 1-4.

Each of the vessels 1 and 2 is also provided with a gas supply tube 5 and 6 through which gases may enter or leave the vessels. The gas supply tubes 5 and 6 are in turn connected to valves 7 and 8 which are adapted for connection to a source of gas, preferably an inert gas such as nitrogen or argon, or vacuum. In the case where a plurality of vessel pairs are combined in a single apparatus, manifolds 10 may be interposed between gas supply tubes 5 and 6 and valves 7 and 8.

Finally, the apparatus shown in FIGS. 1-4 includes a dosing device 9 connected to a dosing tube 9 which is used to provide polymerase or other reagents to the polymerization vessel 1.

Looking now to the operation of the apparatus in the method of the invention, FIG. 1 shows the apparatus in a configuration suitable for the polymerization step. Thus, polymerization vessel 1 contains a reaction mixture 100 which comprises single stranded target nucleic acids, suitable primers, polymerase enzyme and nucleoside triphosphates. The temperature in polymerization vessel 1 is maintained by thermoregulator means 11 at a level at which polymerization occurs. During this stage of the method, both valves 7 and 8 are preferably in the deactivated or vent position such that the interiors of vessels 1 and 2 are at atmospheric pressure.

After polymerization is substantially complete, the reaction mixture 100 is transferred from the polymerization vessel 1 to the denaturation vessel 2 via liquid transfer tube 3. This can be accomplished by closing valve 7 such that gas flows from tube 14 through valve 7 into polymerization vessel 1 through gas supply tube 5. Because valve 8 remains in the vent position, reaction mixture 100 is forced through liquid transfer tube 3 and into the denaturation vessel 2. Suitable gas pressures are from 0.1 to 1.0 atm above ambient. It will of course be understood that this type of fluid transfer system requires that the vessels be air tight when the valves 7 and 8 are in other than the vent position.

Figure 3:
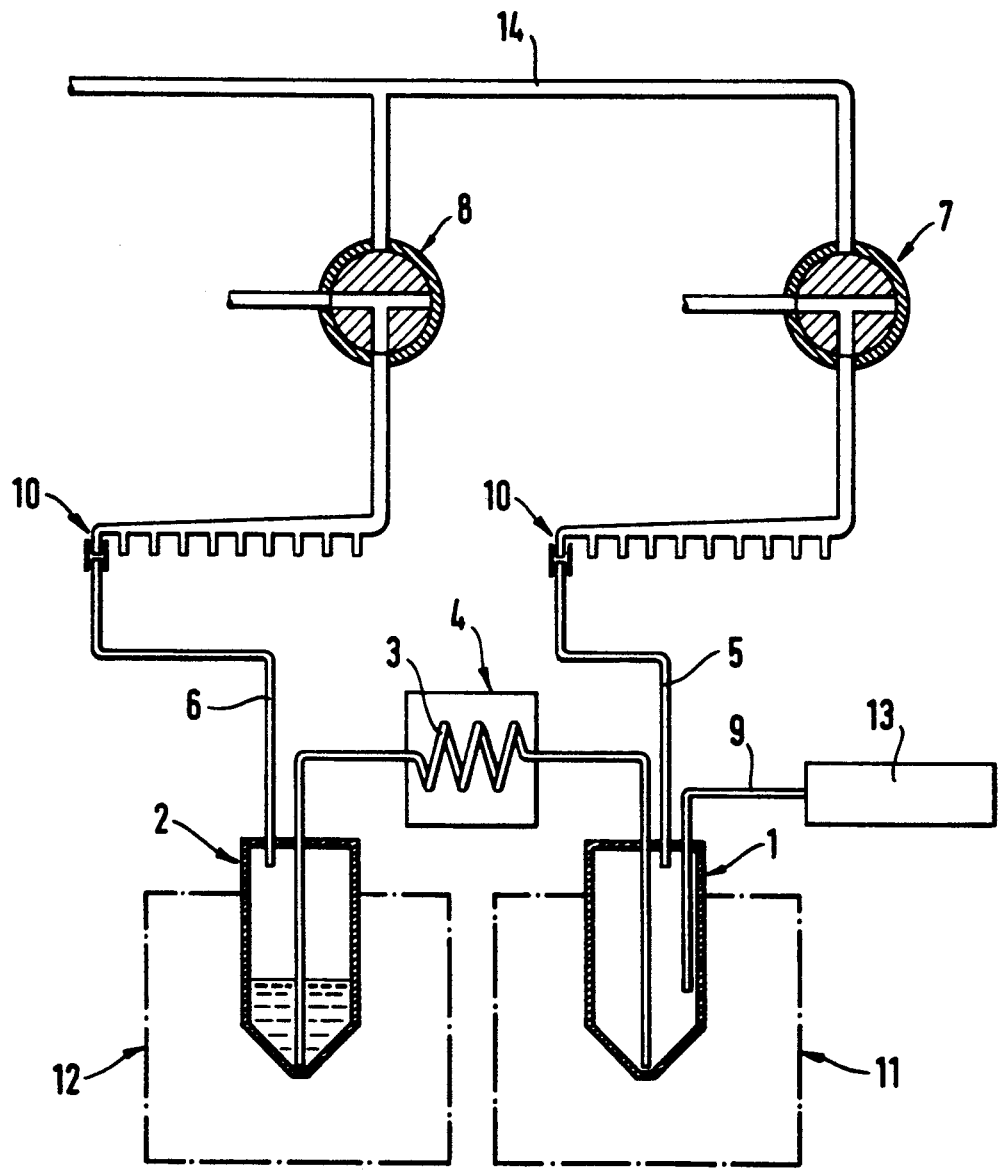
FIG. 3 depicts an apparatus according to the invention during the step of denaturation of DNA.

After the transfer of reaction mixture is complete, the reaction mixture 100 is incubated in the denaturation vessel 2 for a period of time to allow substantially complete denaturation of double stranded nucleic acids to single stranded nucleic acid. During this incubation, and indeed throughout the entire process, the temperature of the denaturation vessel 2 is maintained at a temperature suitable for denaturation by thermoregulator means 12. Valves 7 and 8 are again preferably in the vent position to preclude liquid transfer (FIG. 3).

Figure 4:
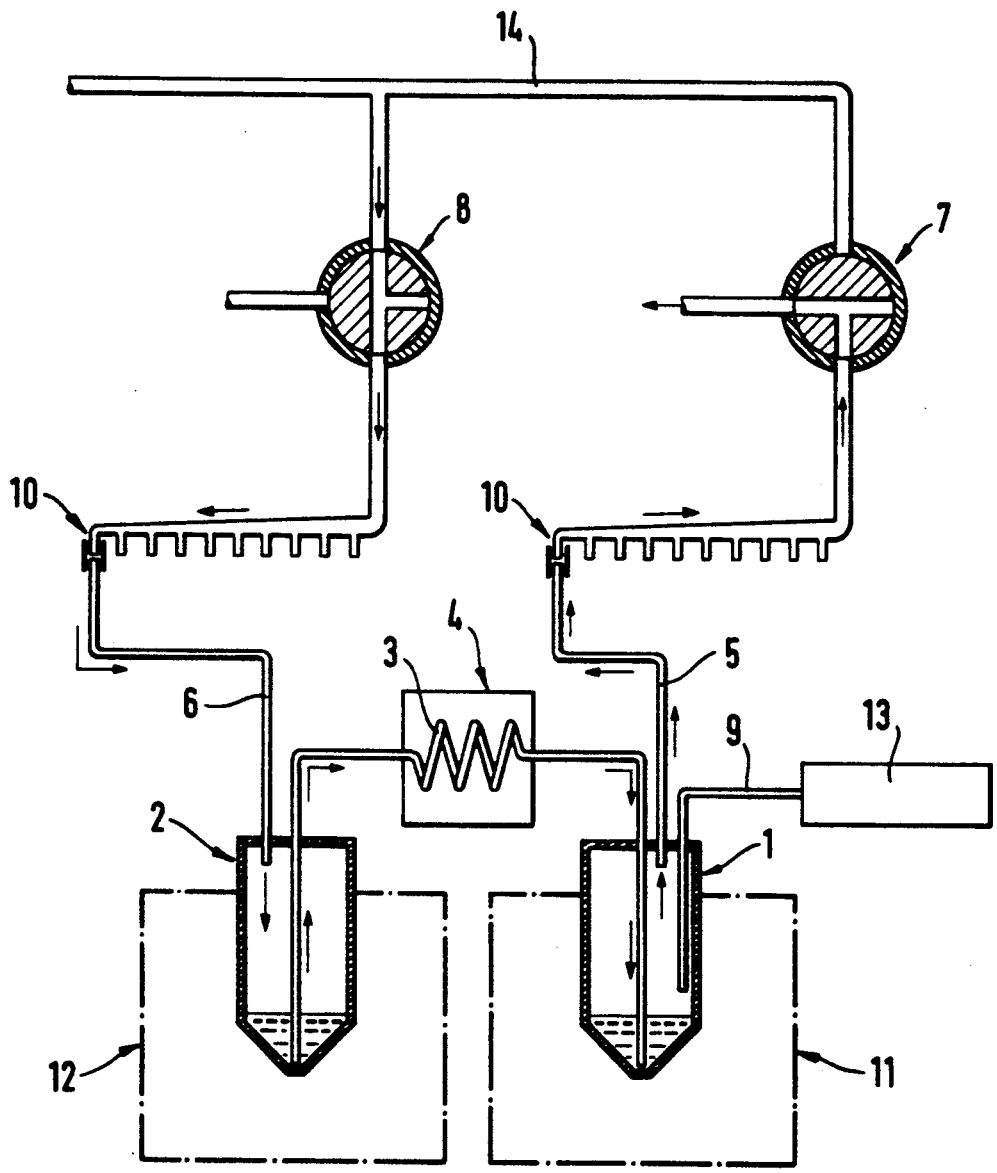
FIG. 4 depicts an apparatus according to the invention during the transferring of the fluid back into the polymerization vessel.

Finally, after the denaturation step, the reaction mixture 100 is transferred back to the polymerization vessel 1 via liquid transfer tube 3 (FIG. 4). Preferably, liquid transfer tube 3 passes through a heat exchanger 4 which rapidly lowers the temperature to one at which hybridization of nucleic acids is favored. This allows the primers and the partially amplified target nucleic acids to be annealed prior to their return to the polymerization vessel 1 and is particularly advantageous when the optimum temperature for the polymerase is not well suited to hybridization. It also prevents denaturation of polymerase resulting from pouring hot reaction mixture into the polymerization vessel 1. The transfer of reaction mixture 100 from denaturation vessel 2 to polymerization vessel 1 is accomplished by closing valve 8 to introduce a flow of gas into denaturation vessel 2 through gas supply tube 6 while valve 7 is in the vent position.

The valves which control the flow of gas and thus the transfer of the reaction mixture between the vessels are preferably automatically controlled. For example, microprocessors can be used to control the operation of magnetic three-way valves to make the amplification process automated, since the steps depicted in FIGS. 1-4 can be repeated several, even tens of times under microprocessor control. In the preferred embodiment the steps are repeated a suitable number of times to yield enough amplified DNA for a specific end use. The amplification therefore occurs automatically from beginning to end.

The invention is not limited to the embodiment described above and depicted in FIGS. 1-4 and variations are possible within the scope of the claimed invention. In the apparatus described above it is possible to use a vacuum or other means instead of elevated gas pressure for transfer of the liquids. For example, the reaction mixture can also be transferred from one vessel to the other by means of a fluid pump, in which case the gas tubes 5 and 6 are not necessary. In such a case it is possible to use a pump with a reversible flow direction, in which case only one liquid transfer tube 3 is required between the vessels 1 and 2. An amplification apparatus in which the transfer of liquid is effected by means of elevated pressure or a vacuum is preferred, however, since it conveniently enables several target nucleic acid mixtures to be treated simultaneously in parallel vessel pairs. In such an apparatus, a single pair of valves can be used for controlling the transfer of the reaction mixtures in all vessel pairs from one vessel to the other using manifolds 10 as shown.

It should also be understood that heat exchanger 4 is optional. The same cooling effect might be achieved by using a longer liquid transfer tube 3, or may be unnecessary if the polymerization temperature is suitable for hybridization as well.

The above amplification of nucleic acids can also be performed on complementary DNA obtained from ribonucleic acid by using a reverse transcriptase.

The series of amplification reactions is preferably started with the step according to FIG. 1, i.e. the reagents necessary for the amplification and a single-stranded target nucleic acid are incubated at the optimum temperature for the optimum period in order to perform the polymerase reaction. If the target nucleic acid is originally double-stranded, it is rendered single-stranded before the first step. It is, of course, possible to use the amplification apparatus for the denaturation of the target nucleic acid, in which case the whole reaction series is started with the step depicted in FIG. 3. In this case it is in general advantageous to use a longer denaturation period than during actual amplification.

The optimum temperatures and times to be used in the reaction series are determined on the basis of the target nucleic acid, as well as the primer and polymerase used. A person skilled in the art is able to adjust the apparatus and to select the suitable conditions for the amplification reactions to be performed at a given time.

A number of different procedures are possible with respect to the addition of the polymerase. The enzyme may be introduced either continuously or intermittently by automatic means into the polymerase reaction vessel. If the enzyme is thermostable, it is incorporated into the reaction mixture at the beginning of the reaction series and added thereafter only when needed. No enzyme needs to be added if it has been introduced into the polymerase reaction vessel either in an immobilized form or in a suitable slowly releasing dosage form. If the enzyme is immobilized, it of course does not pass from the reaction vessel. When a slowly releasing dosage form is used, it is important that the release of the polymerase is regulated so that its concentration remains suitable for the duration of as many reaction cycles as is necessary.

The temperature of the heat exchanger is determined by the hybridization temperature of the primer to the single-stranded DNA. When the hybridization temperature of the primer differs considerably from the optimum temperature of the polymerization enzyme, the temperature profile of the reaction mixture is preferably regulated so that the primer and single-stranded DNA have time to hybridize in the heat exchanger. The thermolability of the polymerization enzyme can also be taken into consideration in the regulation of the heat exchanger by making sure that the reaction mixture is cooled sufficiently before it comes into contact with the enzyme. The retention time in the heat exchanger of the solution which contains the denatured nucleic acid can be regulated by means of the tube length and the pressure of the gas introduced into the denaturation vessel, or respectively by adjusting the vacuum or the efficiency of the fluid pump.

We claim:

1. An apparatus for use in amplification of nucleic acids comprising at least one pair of reaction vessels, each pair of vessels including a polymerization vessel and a denaturation vessel; first thermoregulation means connected to the denaturation vessel such that the denaturation vessel can be maintained at an appropriate temperature for denaturation of double stranded nucleic acids; second thermoregulation means connected to the polymerization vessel such that the polymerization vessel can be maintained at an appropriate temperature for polymerization of nucleic acids; and a liquid transfer system which interconnects the vessels by means of at least one liquid transfer tube extended from within the denaturation vessel to within the polymerization vessel and which is effective to transfer liquid form the denaturation vessel to the polymerization vessel and from the polymerization vessel to the denaturation vessel, said liquid transfer system further comprising a pump with a reversible flow direction which in combination with the liquid transfer tubes is effective to transfer liquid between the vessels.

2. The apparatus according to claim 1, wherein the pump is microprocessor controlled.

3. The apparatus according to claim 1, wherein the liquid transfer system further comprises means for creating a pressure differential between the polymerization vessel and the denaturation vessel such that liquid is transferred between the vessels.

4. The apparatus according to claim 3, wherein the liquid transfer system is connectable to a gas source for selectively introducing a flow of a gas into one of the pair of reaction vessels by means of at least one gas supply tube.

5. The apparatus according to claim 3, wherein the liquid transfer system is connectable to a vacuum source for selectively creating a reduced pressure in one of the pair of reaction vessels by means of at least one gas supply tube.

6. The apparatus according to claim 4, wherein the gas is an inert gas.

7. The apparatus according to claim 4, wherein the flow of gas is regulated by at least one valve.

8. The apparatus according to claim 7, further comprising means for automatically cycling the valve between open and closed positions.

9. The apparatus according to claim 8, wherein the means for automatically cycling the valve is a microprocessor.

10. The apparatus according to claim 4, wherein the gas source is constructed so as to provide the gas flow at a pressure of between 0.1 and 1.0 atmospheres above ambient.

11. The apparatus according to claim 7, comprising means for automatically controlling the reduction of pressure in the vessels.

12. The apparatus according to claim 11, wherein the means for automatically controlling the reduction of pressure is a microprocessor.

13. The apparatus according to claim 1, further comprising cooling means positioned between the denaturation vessel and the polymerization vessel.

14. The apparatus according to claim 13, wherein the cooling means is a heat exchanger.

15. The apparatus according to claim 1, further comprising means for adding reagents to at least one of the denaturation vessel and the polymerization vessel.

16. The apparatus according to claim 1, wherein the means for adding liquids is a dosing device.

17. The apparatus according to claim 16, wherein the dosing device is operated by an automatic control device.

* * * * *

UNITED STATES PATENT AND TRADEMARK OFFICE
CERTIFICATE OF CORRECTION

PATENT NO. : 5,133,940

DATED : July 28, 1992

INVENTOR(S) : Kalkkinen et al

It is certified that error appears in the above-identified patent and that said Letters Patent is hereby corrected as shown below:

Title page, in the Abstract item [57], line 5, "deoxyribouncleoside" should read --deoxyribonucleoside--; line 6, "polymerication" should read --polymerization--; and line 14, "denaaturation" should read --denaturation--.

Column 3, line 52, "device 9" should read --device 13--.

Column 6, line 49, "claim 7" should read --claim 5--.

Signed and Sealed this

Thirtieth Day of November, 1993

Attest:

BRUCE LEHMAN

Attesting Officer     Commissioner of Patents and Trademarks